US009540355B2

(12) United States Patent
Smith, III et al.

(10) Patent No.: US 9,540,355 B2
(45) Date of Patent: Jan. 10, 2017

(54) IRCINIASTATIN ANALOGUES

(71) Applicant: The Trustees of The University of Pennsylvania, Philadelphia, PA (US)

(72) Inventors: Amos B. Smith, III, Merion, PA (US); Chihui An, Philadelphia, PA (US); Adam T. Hoye, Bala Cynwyd, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/761,030

(22) PCT Filed: Jan. 15, 2014

(86) PCT No.: PCT/US2014/011610
§ 371 (c)(1),
(2) Date: Jul. 15, 2015

(87) PCT Pub. No.: WO2014/113427
PCT Pub. Date: Jul. 24, 2014

(65) Prior Publication Data
US 2015/0344462 A1 Dec. 3, 2015

Related U.S. Application Data

(60) Provisional application No. 61/752,508, filed on Jan. 15, 2013.

(51) Int. Cl.
*C07D 407/06* (2006.01)
*A61K 31/352* (2006.01)

(52) U.S. Cl.
CPC .................................. *C07D 407/06* (2013.01)

(58) Field of Classification Search
CPC ............................ C07D 407/06; A61K 31/352
See application file for complete search history.

(56) References Cited

U.S. PATENT DOCUMENTS

| 7,439,265 B2 | 10/2008 | Pettit et al. |
| 2007/0015821 A1 | 1/2007 | Brabander et al. |
| 2007/0135516 A1 | 6/2007 | Pettit |

FOREIGN PATENT DOCUMENTS

| WO | WO 2009-158381 | 12/2009 |
| WO | WO 2010/022148 | 2/2010 |

OTHER PUBLICATIONS

Huang et al (2009): STN International HCAPLUS database, (Columbus, Ohio), Accession No. 2009:1618859.*
Berge et al, "Pharmaceutical Salts", Journal of Pharmaceutical Sciences, Jan. 1977, 66(1),1-19.
Burres et al, "Antitumor Activity and Mechanism of Action of the Novel Marine Natural Products Mycalamide-A and -B and Onnamide", Cancer Research, Jun. 1, 1989, 49(11), 2935-2940.
Feng et al, "Studies toward the Unique Pederin Family Member Psymberin: Full Structure Elucidation, Two Alternative Total Syntheses, and Analogs", Journal of the American Chemical Society, Sep. 24, 2012, 134, 17083-17093.
Hood et al, "Induction of Apoptosis by the Marine Sponge (Mycale) Metabolites, Mycalamide A and Pateamine", Apoptosis, Jun. 2001 6(3), 207-219.
Huang et al, "The Discovery of Potent Antitumor Agent C11-Deoxypsymberin/irciniastatin A: Total Synthesis and Biology of Advanced Psymberin Analogs", Organic Letters, Feb. 19, 2009, 11(4), 867-870.
International Application No. PCT/US14/11610: International Search Report and the Written Opinion dated Apr. 30, 2014, 14 pages.
Kobayashi et al, "Three New Onnamide Congeners from the Okinawan Marine Sponge *Theonella* Sp.", Journal of Natural Products, Jun. 1993, 56(6), 976-981.
Paul et al, "Theopederins K and L. Highly Potent Cytotoxic Metabolites From a Marine Sponge *Discodermia* Species", Journal of Natural Products, Jan. 2002, 65 (1), 59-61.
Pettit et al, "Antineoplastic Agents. 520. Isolation and Structure of Irciniastatins A and B from the Indo-Pacific Marine Sponge Ircinia Ramosa1", Journal of Medicinal Chemistry, Feb. 2004, 47(5), 1149-1152.
Robinson et al, "Probing the Bioactive Constituents From Chemotypes of the Sponge Psammocinia aff. Bulbosa", Journal of Natural Products, Jun. 2007, 70(6),1002-1009.
West et al, "Mycalamide D, a New Cytotoxic Amide from the New Zealand Marine Sponge *Mycale* Species", Journal of Natural Products, Mar. 4, 2000, 63(5), 707-709.
Wu et al, "Studies Toward the Unique Pederin Family Member Psymberin: Structure Activity Relationships, Biochemical Studies and Genetics Identify the Mode of Action of Psymberin", Journal of the American Chemical Society, Nov. 21, 2012, 134(46), 18998-19003.

* cited by examiner

*Primary Examiner* — Golam M M Shameem
(74) *Attorney, Agent, or Firm* — Baker & Hostetler LLP

(57) ABSTRACT

The present invention is directed to irciniastatin analogs. Uses of these analogs also described.

21 Claims, No Drawings

IRCINIASTATIN ANALOGUES

CROSS-REFERENCE TO RELATED APPLICATIONS

This application is the National Stage of International Application No. PCT/US2014/011610, filed Jan. 15, 2014, which claims the benefit of U.S. Provisional Application No. 61/752,508, filed Jan. 15, 2013, the entire disclosures of both of which are incorporated herein by reference.

GOVERNMENT RIGHTS

The subject matter disclosed herein was made with government support under the National Institutes of Health (National Cancer Institute) under Grant No. CA-19033. The Government has certain rights in the herein disclosed subject matter.

FIELD OF THE INVENTION

The present invention is directed to irciniastatin analogues and methods of their use.

BACKGROUND OF THE INVENTION

In 2004, the laboratories of Pettit and coworkers first published the isolation, structural elucidation, and biological activity of (+)-irciniastatin A and (−)-irciniastatin B. Pettit, G. R.; Xu, J. P.; Chapuis, J. C.; Pettit, R. K.; Tackett, L. P.; Doubek, D. L.; Hooper, J. N. A.; Schmidt, J. M. *Journal of Medicinal Chemistry* 2004, 47, 1149-1152. Pettit and coworkers first collected samples containing irciniastatins A and B from the Indo-Pacific marine sponge *Ircinia ramosa* near Samporna, Borneo in 1991. The dichloromethane-methanol extracts exhibited strong activity ($GI_{50}=10^{-2}$ µg/mL) against the P388 murine lymphocytic leukemia cancer cell line. Unfortunately, recollection on a larger scale to allow for isolation of the individual constituents was not permitted (political obstacles) and so the extracts were preserved for later use. As isolation techniques advanced over the past decade, irciniastatins A and B were isolated as an individual constituent (34.7 mg and 2.2 mg, respectively) from the initial dichloromethane-methanol extracts.

After isolating irciniastatins A and B, Pettit and coworkers tested the compound against cancer cell lines, including the P388 murine lymphocytic leukemia cell line and human umbilical vein endothelial cells (HUVEC) (Table 1.1). Id.

TABLE 1.1

Growth Inhibition of Cancer Cell Lines ($GI_{50}$, µg/mL) by Irciniastatins A and B

| Cancer Cell Line | | Irciniastatin A | Irciniastatin B |
|---|---|---|---|
| pancreas | BXPC-3 | 0.0038 | 0.00073 |
| breast | MCF-7 | 0.0032 | 0.0005 |
| CNS | SF-268 | 0.0034 | 0.00066 |
| lung | NCI-H460 | <0.0001 | 0.0012 |
| colon | KM20L2 | 0.0027 | 0.0021 |
| prostate | DU-145 | 0.0024 | 0.0016 |
| leukemia | P388 | 0.00413 | 0.006 |
| normal endothelial | HUVEC | <0.0005 | ND |

Additionally, (+)-irciniastatin A was evaluated against the panel of 60 human cancer cell lines within the NCI Developmental Therapeutics in Vitro Screening Program (Table 1.2).

TABLE 1.2

Differential Sensitivities ($LC_{50}$) of Several NCI 60 Cell Lines to (+)-Irciniastatin A

| Cell Line | $LC_{50}$ (M) | Cell Line | $LC_{50}$ (M) |
|---|---|---|---|
| leukemia | | melanoma | |
| CCRF-CEM | $>2.5 \times 10^{-5}$ | LOX IMVI | $>2.5 \times 10^{-5}$ |
| HL-60(TB) | $>2.5 \times 10^{-5}$ | MALME-3M | $<2.5 \times 10^{-9}$ |
| K-562 | $>2.5 \times 10^{-5}$ | SK-MEL-2 | $>2.5 \times 10^{-5}$ |
| MOLT-4 | $>2.5 \times 10^{-5}$ | SK-MEL-5 | $<2.5 \times 10^{-9}$ |
| RPMI-8226 | $>2.5 \times 10^{-5}$ | UACC-257 | $>2.5 \times 10^{-5}$ |
| SR | $>2.5 \times 10^{-5}$ | UACC-62 | $<2.5 \times 10^{-9}$ |
| breast cancer | | colon cancer | |
| MCF7 | $>2.5 \times 10^{-5}$ | HCC-2998 | $3.6 \times 10^{-7}$ |
| HS 578T | $>2.5 \times 10^{-5}$ | HCT-116 | $<2.5 \times 10^{-9}$ |
| MDA-MB-435 | $<2.5 \times 10^{-9}$ | HT29 | $>2.5 \times 10^{-5}$ |
| NCI/ADR-RES | $1.9 \times 10^{-5}$ | SW-620 | $>2.5 \times 10^{-5}$ |
| T-47D | $1.36 \times 10^{-5}$ | | |

(+)-Irciniastatin A exhibits activities in the low nanomolar range for the MDA-MB-35 breast cancer, SK-MEL-28 and UACC-62 melanoma, and the HCT-116 colon cancer cell lines with an activity differential of greater than 10,000-fold as compared to other cell lines within their respective subsets. Burres, N. S.; Clement, J. *J. Cancer Res.* 1989, 49, 2935-2940; Kobayashi, J. I.; Itagaki, F.; Shigemori, H.; Sasaki, T. *Journal of Natural Products* 1993, 56, 976-981; West, L. M.; Northcote, P. T.; Hood, K. A.; Miller, J. H.; Page, M. J. *Journal of Natural Products* 2000, 63, 707-709; Hood, K. A.; West, L. M.; Northcote, P. T.; Berridge, M. V.; Miller, J. H. *Apoptosis* 2001, 6, 207-219; Paul, G. K.; Gunasekera, S. P.; Longley, R. E.; Pomponi, S. A. *Journal of Natural Products* 2002, 65, 59-61.

(+)-Irciniastatin A was also evaluated in the NCI Developmental Therapeutics Program hollow fiber assay using several solid tumor cell lines resulting in an overall score of 34 (compounds considered active score 20 or higher), based on scores of 28 against intraperitoneal fibers and 6 against subcutaneous fibers. Robinson, S. J.; Tenney, K.; Yee, D. F.; Martinez, L.; Media, J. E.; Valeriote, F. A.; vanSoest, R. W. M.; Crews, P. *Journal of Natural Products* 2007, 70, 1002-1009.

Analogues of irciniastatin have been only sparingly investigated. For example, De Brander prepared analogues to investigate the bioactivity where the psymberate (C-1 to C-8) and didhydroisocoumarin side chains were altered.

Various compounds prepared and evaluated by De Brander et al.

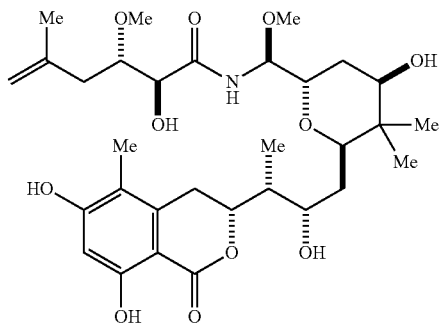

1a: R = H, psymberim
1b: R = Ac
1c: R = Me

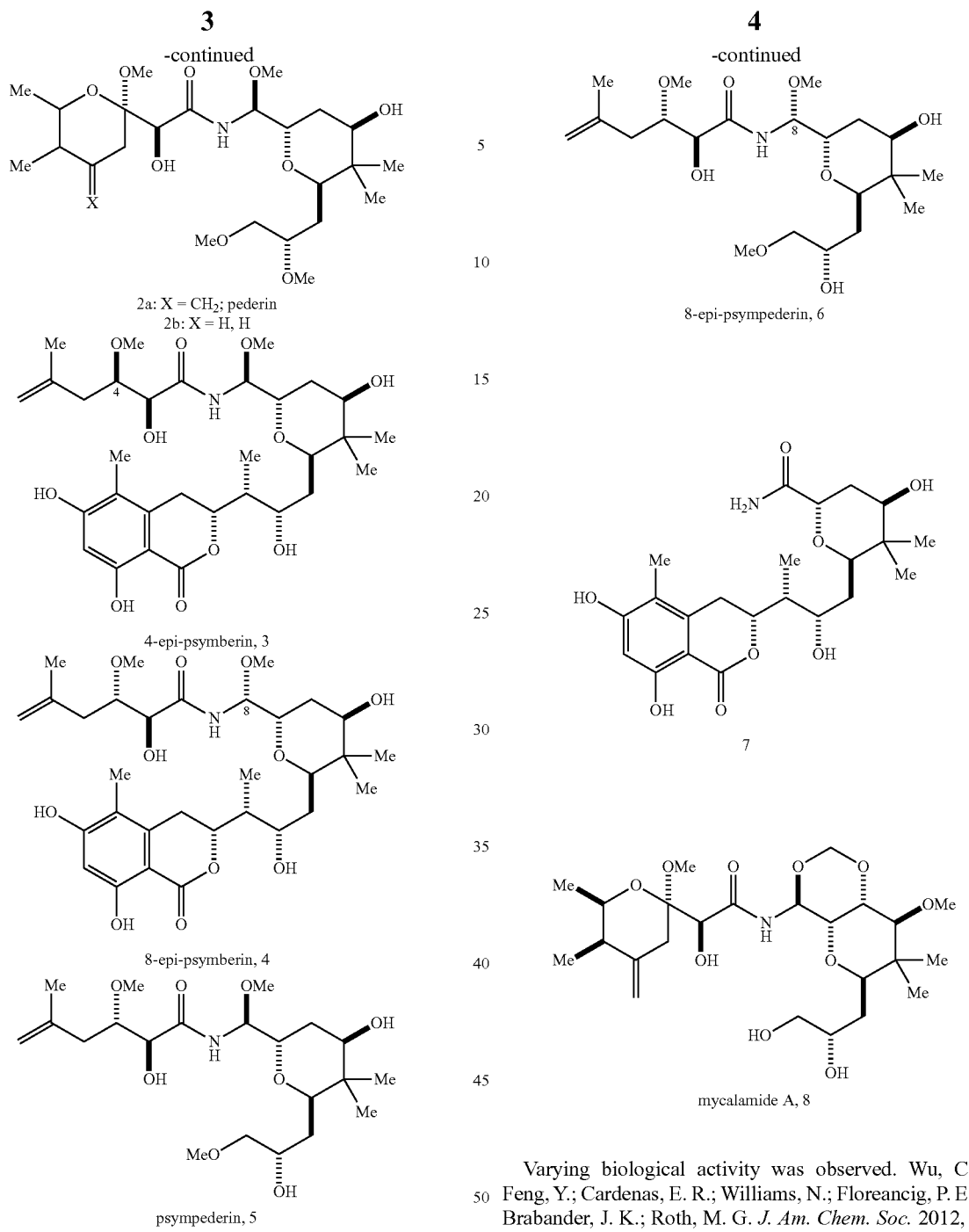

Varying biological activity was observed. Wu, C. Y.; Feng, Y.; Cardenas, E. R.; Williams, N.; Floreancig, P. E.; De Brabander, J. K.; Roth, M. G. *J. Am. Chem. Soc.* 2012, 134, 18998-19003.

TABLE 1.3

Cytotoxicity[a] and Translation Inhibition of Analogues of Irciniastatin

|  | cytotoxicity (IC$_{50}$ nM) | | translation inhibition (EC$_{50}$ nM)[a] | | |
|---|---|---|---|---|---|
|  | | | in vitro assay | cell-based assay | |
| compound | Hela[c] | SK-MEL-S[d] | | Hela | SK-MEL-S |
| cycloheximide | 2292 ± 1525 | 3126 ± 764 | 3150 ± 2352 | 3325 ± 434 | 2670 |
| 1a | 0.64 ± 0.14 | 0.27 ± 0.04 | 28 ± 7 | 22 ± 1.4 | 33 ± 10 |
| 1b | 0.54 ± 0.01 | 0.35 ± 0.07 | 342 ± 21 | 5.8 ± 1.7 | 4.2 ± 5.2 |
| 1c | 2.34 ± 0.53 | 1.58 ± 0.42 | 320 ± 47 | 9.6 ± 8.9 | 9.3 ± 8.5 |
| 8 | 2.52 ± 1.39 | 3.79 ± 0.04 | 238 ± 44 | 59 ± 32 | 64 |
| 3 | 613.6 ± 267.0 | 352.0 ± 12.1 | 346 ± 64 | 4950 ± 4870 | 495 |

TABLE 1.3-continued

Cytotoxicity[a] and Translation Inhibition of Analogues of Irciniastatin

| | cytotoxicity (IC$_{50}$ nM) | | translation inhibition (EC$_{50}$ nM)[a] | | |
|---|---|---|---|---|---|
| | | | in vitro assay | cell-based assay | |
| compound | Hela[c] | SK-MEL-S[d] | | Hela | SK-MEL-S |
| 4 | >1000 | 762.8 ± 70.0 | 318 ± 182 | 2200 ± 1410 | 843 |
| 5 | >1000 | >1000 | 641 ± 262 | 1650 ± 1060 | 578 |
| 6 | >1000 | >1000 | >10 000 | >10 000 | >10 000 |
| 7 | >1000 | >1000 | >10 000 | >10 000 | >10 000 |

[a] A CellTiter-Glo luminescent assay, which measures cellular ATP concentrations, was used to measure cell viability with and without compound treatment. IC$_{50}$ values were calculated by fitting the luminescence data to an equation representing the dose-response of inhibiting luminescence.
[b] Data are means ± standard deviation from at least two independent experiments conducted as triplicate.
[c] R2 values range from 0.931 to 0.994.
[d] R2 values range from 0.865 to 0.997.
[e] R2 ranges from 0.90 to 0.995.

Huang et al. also prepared analogues by altering the psymberate side chain. Additionally, the C11-deoxyirciniastatin demonstrated 3 to 10 times the potency of irciniastatin against various cancer types. Huang, X.; Shao, N.; Huryk, R.; Palani, A.; Aslanian, R.; Seidel-Dugan, C. *Org. Lett.* 2009, 11, 867-870.

TABLE 1.4

Anticancer Activity of C11-Deoxyirciniastatin and its Epimers[a]

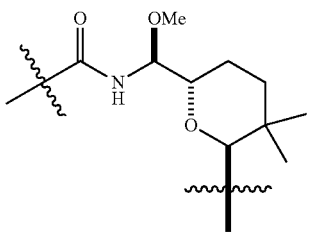 [SMILES: *C(=O)N[C@@H](OC)[C@@H]1CCC(C)(C)[C@@H](*)O1]
29

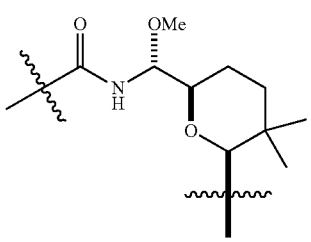 [SMILES: *C(=O)N[C@H](OC)[C@H]1CCC(C)(C)[C@@H](*)O1]
29a

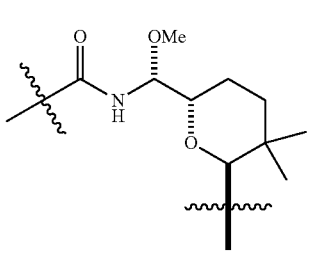 [SMILES: *C(=O)N[C@H](OC)[C@@H]1CCC(C)(C)[C@@H](*)O1]
29b

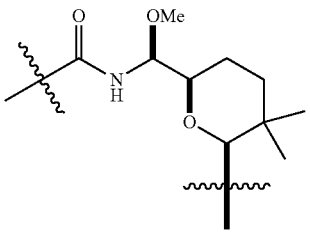 [SMILES: *C(=O)N[C@@H](OC)[C@H]1CCC(C)(C)[C@@H](*)O1]
29c

| 29 (IC$_{50}$ nM) | 29a (IC$_{50}$ nM) | 29b (IC$_{50}$ nM) | 29c (IC$_{50}$ nM) | cell line | human tissue type |
|---|---|---|---|---|---|
| 0.265 ± 0.008 | n.d. | n.d. | 8.7 ± 0.18 | ACHN | kidney |
| 0.149 ± 0.005 | n.d. | n.d. | 5.9 ± 0.18 | DU145 | prostate |
| 0.034 ± 0.004 | n.d. | n.d. | 1.6 ± 0.27 | H226 | lung |
| 0.055 ± 0.002 | 177 ± 6 | 46 ± 7 | 3.0 ± 0.12 | HOP62 | lung |
| 0.142 ± 0.007 | n.d. | n.d. | 5.3 ± 0.15 | MB231 | breast |
| 0.076 ± 0.004 | n.d. | n.d. | 3.9 ± 0.48 | MKN45 | gastric |
| 0.073 ± 0.006 | n.d. | n.d. | 2.9 ± 0.21 | PC3 | prostate |
| 0.160 ± 0.015 | n.d. | n.d. | 6.1 ± 0.22 | SW620 | colon |
| 0.066 ± 0.004 | n.d. | n.d. | 3.8 ± 0.10 | NHDF | normal |

[a] The CellTiter-Glo Luminescent Cell Viability Assay (Promega, Technical bulletin 288) was employed in this study. IC$_{50}$ data are the mean value of three experiments with statistical significance calculated.

However, the full structure-activity relationship is not fully developed and there is a need for more irciniastatin analogues.

SUMMARY OF THE INVENTION

The present invention provides compositions for a compound of Formula I, or a stereoisomer thereof,

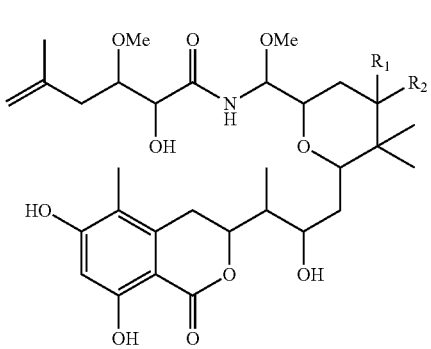
I wherein

R$_1$ is hydrogen; and

R$_2$ is halogen, O—C(O)phenyl, O—C(O)C$_{1-6}$alkyl, OC$_{1-6}$ alkyl; or C$_{1-6}$ alkyl, or wherein R$_1$ and R$_2$ together form =CR$_3$R$_4$ or =NR$_5$ wherein R$_3$ and R$_4$ are independently hydrogen or C$_{1-6}$ alkyl, and R$_5$ is O—C$_{1-6}$ alkyl;

or a pharmaceutically acceptable salt thereof

Pharmaceutical compositions and methods of using the compounds of the invention are also described.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

TERMS

The term "pharmaceutically acceptable salt" as used herein refers to those acid addition salts of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. Also included are those salts derived from non-toxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, propionate, pivalate, cyclamate, isethionate, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, e.g., Berge S. M., et al., *Pharmaceutical Salts, J. Pharm. Sci.* 66:1-19 (1977)).

The term "pharmaceutically acceptable" as used herein means does not cause unacceptable loss of pharmacological activity or unacceptable adverse side effects. Examples of pharmaceutically acceptable components are provided in The United States Pharmacopeia (USP), The National Formulary (NF), adopted at the United States Pharmacopeial Convention, held in Rockville, Md. in 1990 and FDA Inactive Ingredient Guide 1990, 1996 issued by the U.S. Food and Drug Administration (both are hereby incorporated by reference herein, including any drawings). Other grades of solutions or components that meet necessary limits and/or specifications that are outside of the USP/NF may also be used.

The term "pharmaceutical composition" as used herein means a composition that is made under conditions such that it is suitable for administration to humans, e.g., it is made under GMP conditions and contains pharmaceutically acceptable excipients, e.g., without limitation, stabilizers, bulking agents, buffers, carriers, diluents, vehicles, solubilizers, and binders. As used herein pharmaceutical composition includes but is not limited to a pre-lyophilization solution or dispersion as well as a liquid form ready for injection or infusion after reconstitution of a lyophilized preparation.

A "pharmaceutical dosage form" as used herein means the pharmaceutical compositions disclosed herein being in a container and in an amount suitable for reconstitution and administration of one or more doses, typically about 1-2, 1-3, 1-4, 1-5, 1-6, 1-10, or about 1-20 doses. Preferably, a "pharmaceutical dosage form" as used herein means a lyophilized pharmaceutical composition disclosed herein in a container and in an amount suitable for reconstitution and delivery of one or more doses, typically about 1-2, 1-3, 1-4, 1-5, 1-6, 1-10, or about 1-20 doses. The pharmaceutical dosage form can comprise a vial or syringe or other suitable pharmaceutically acceptable container. The pharmaceutical dosage form suitable for injection or infusion use can include sterile aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The prevention of the growth of microorganisms can be accomplished by various antibacterial and antifungal agents, for example, parabens, chlorobutanol, phenol, sorbic acid, thimerosal, and the like.

As used herein, the term "excipient" means the substances used to formulate active pharmaceutical ingredients (API) into pharmaceutical formulations; in a preferred embodiment, an excipient does not lower or interfere with the primary therapeutic effect of the API. Preferably, an excipient is therapeutically inert. The term "excipient" encompasses carriers, diluents, vehicles, solubilizers, stabilizers, bulking agents, and binders. Excipients can also be those substances present in a pharmaceutical formulation as an indirect or unintended result of the manufacturing process. Preferably, excipients are approved for or considered to be safe for human and animal administration, i.e., GRAS substances (generally regarded as safe). GRAS substances are listed by the Food and Drug administration in the Code of Federal Regulations (CFR) at 21 CFR §182 and 21 CFR §184, incorporated herein by reference. Preferred excipients include, but are not limited to, hexitols, including mannitol and the like.

As used herein, the term "alkyl" means a hydrocarbon group up to a total of 20 carbons. Preferably, the alkyl group is between 1 and 10 carbons. More preferably, the alkyl group is between 1 and 6 carbons. The alkyl group may be branched or unbranched. Examples of alkyl groups include methyl, ethyl, propyl, isopropyl, cyclopropyl, butyl, isobutyl, tert-butyl, pentyl, isopentyl, hexyl, and the like.

As used herein, benzoyl ("Bz") refers to the moiety —C(O)-phenyl.

As used herein, acetyl ("Ac") refers to the moiety —C(O)CH$_3$.

The present invention provides compositions for a compound of Formula I, or a stereoisomer thereof,

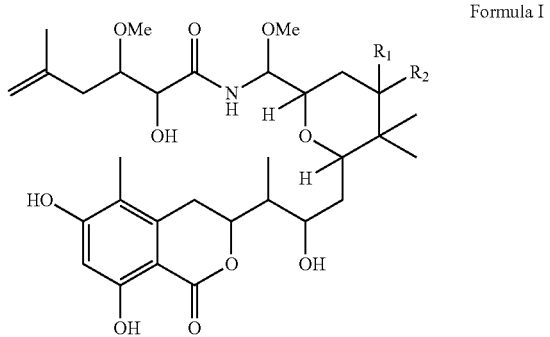

Formula I wherein R$_1$ is hydrogen; and

R$_2$ is halogen, O—C(O)-phenyl, O—C(O)C$_{1-6}$ alkyl, O—C$_{1-6}$ alkyl; or C$_{1-6}$ alkyl, or wherein R$_1$ and R$_2$ together form =CR$_3$R$_4$ or =NR$_5$ wherein R$_3$ and R$_4$ are independently hydrogen or C$_{1-6}$ alkyl, and R$_5$ is O—C$_{1-6}$ alkyl; or a pharmaceutically acceptable salt thereof.

An especially preferred embodiment Formula I is Formula IA.

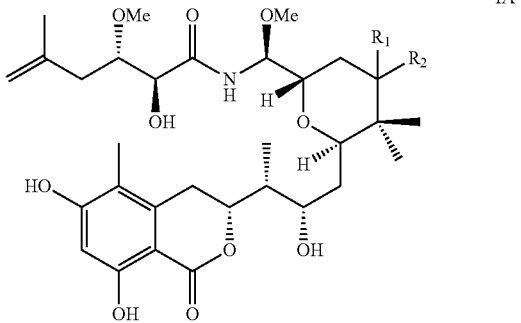

IA

In preferred embodiments, R$_2$ is halogen, that is F, Cl, Br, or I. Particularly preferred embodiments are those wherein R$_2$ is F.

In other embodiments, R$_2$ is —O—C(O)-phenyl. In some embodiments, the phenyl is optionally independently substituted at one, two, three, four, or five positions with, for example, halogen (F, Cl, Br, or I), C$_{1-6}$alkyl, or —OC$_{1-6}$ alkyl.

In yet other embodiments, R$_2$ is —OC(O)C$_{1-6}$ alkyl. Particularly preferred embodiments are those wherein R$_2$ is —OC(O)CH$_3$, —OC(O)-ethyl, —OC(O)-propyl, —OC(O)-cyclopropyl, —OC(O)-butyl, —OC(O)-isobutyl, or —OC(O)-tert-butyl. Particularly preferred embodiments are those wherein R$_2$ is —OC(O)CH$_3$.

In alternate embodiments, R$_2$ is O—C$_{1-6}$ alkyl. Preferred embodiments are those wherein R$_2$ is —Omethyl, —Oethyl, —Opropyl, —Ocyclopropyl, —Obutyl, —Oisobutyl, or —Otert-butyl. Particularly preferred embodiments include those wherein R$_2$ is —Omethyl.

In still other embodiments, R$_2$ is C$_{1-6}$ alkyl. In preferred embodiments, R$_2$ is methyl, ethyl, propyl, cyclopropyl, butyl, isobutyl, or tert-butyl.

In further embodiments of the invention, R$_1$ and R$_2$ together form =CR$_3$R$_4$. In such embodiments, R$_3$ and R$_4$ are independently hydrogen or C$_{1-6}$ alkyl.

In other embodiments, R$_1$ and R$_2$ together form =NR$_5$ wherein R$_5$ is O—C$_{1-6}$ alkyl. Particularly preferred embodiments include those wherein R$_5$ is —Omethyl, —Oethyl, —Opropyl, —Oisopropyl, —Obutyl, —Oisobutyl, or —Otert-butyl.

Especially preferred compounds of the invention are depicted below as compounds (a)-(f).

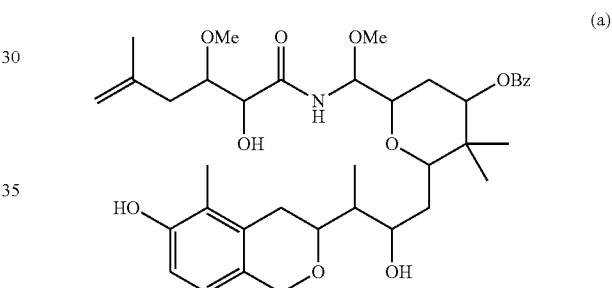

(a)

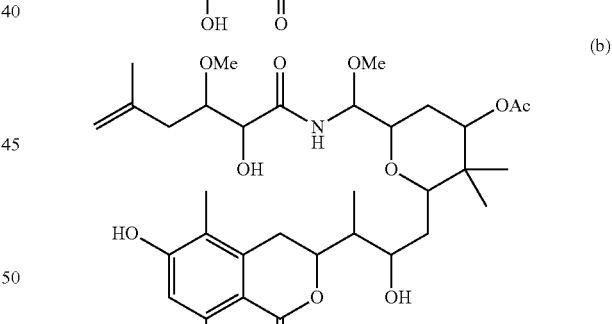

(b)

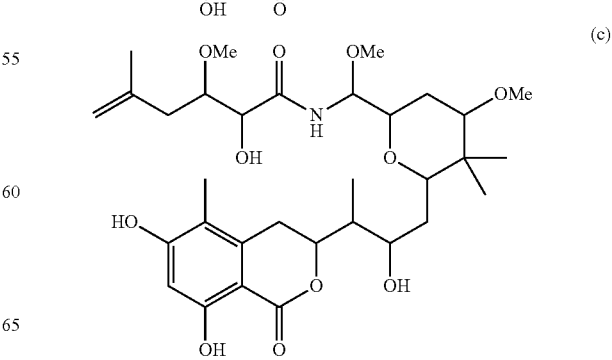

(c)

-continued
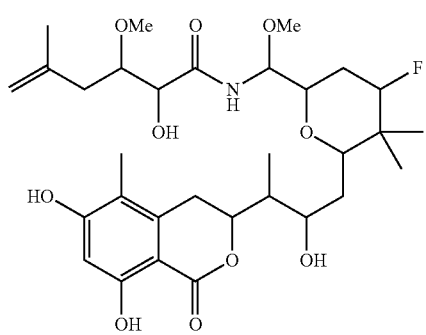
(d)
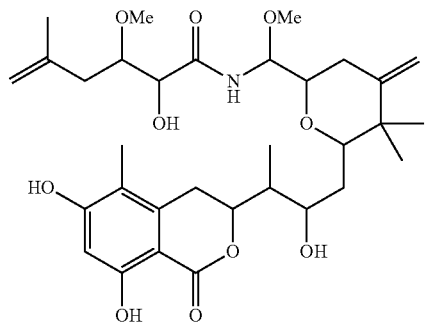
(e)
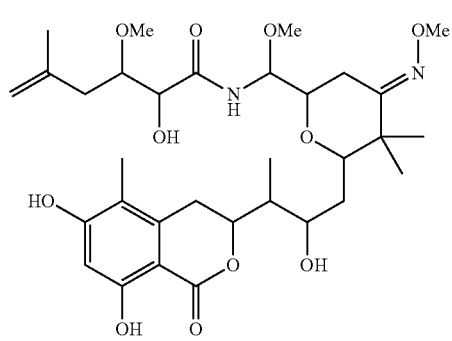
(f)
The compounds of Formula I comprise chiral centers. The compositions may comprise a mixture of stereoisomers or may be resolved in isomerically pure forms using methods known to those skilled in the art.
Particularly preferred stereoisomers of the invention are depicted below as compounds (g)-(l).
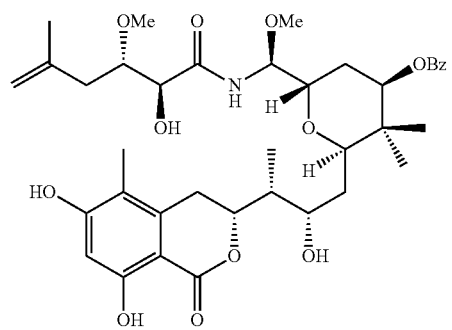
(g)
-continued
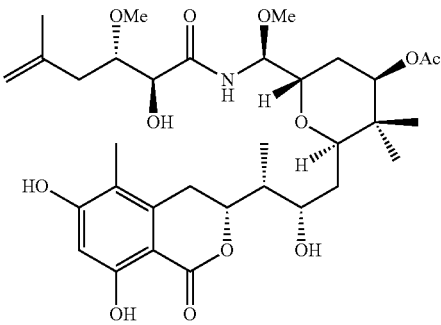
(h)
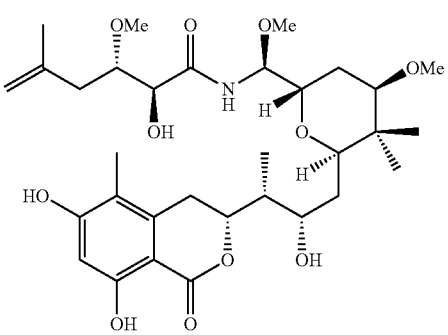
(i)
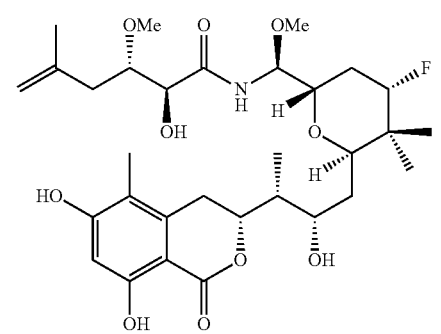
(j)
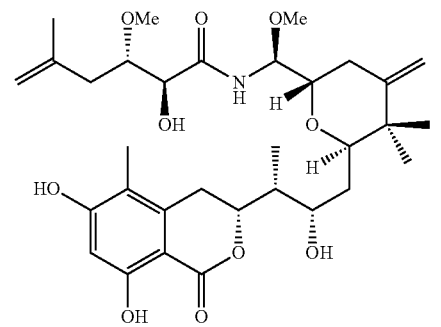
(k)
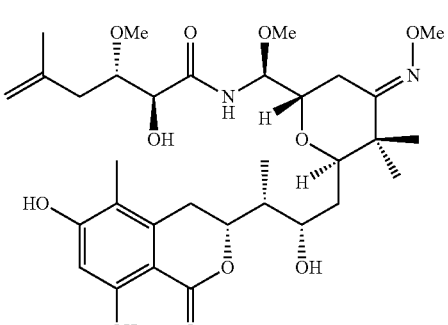
(l)

Compounds of the invention may be prepared, for example, from (+)-Irciniastatin A (m), epi-C(11)-Irciniastatin A (n) or (−)-Irciniastatin B(o), or a stereoisomer thereof:

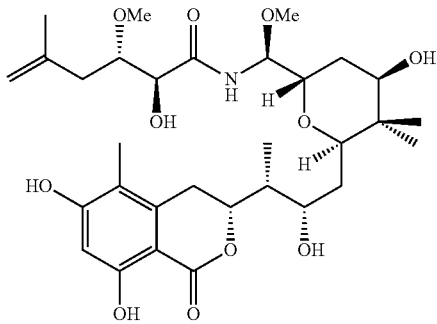
(m)

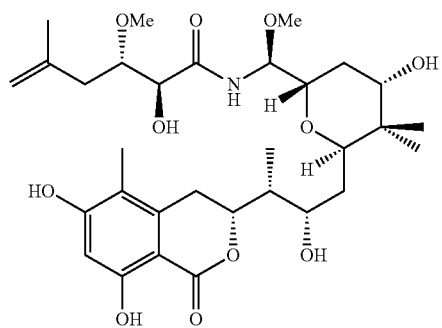
(n)

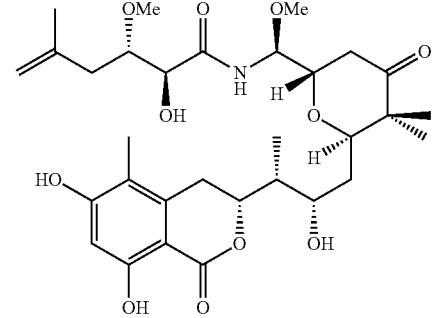
(o)

Compounds of the invention can be prepared according to methods known in the art. Exemplary methods of preparation are described herein.

For example, as seen in Scheme 1, subjecting protected alcohol (m) with benzoyl chloride, followed by deprotection will result in compound (g).

Scheme 1

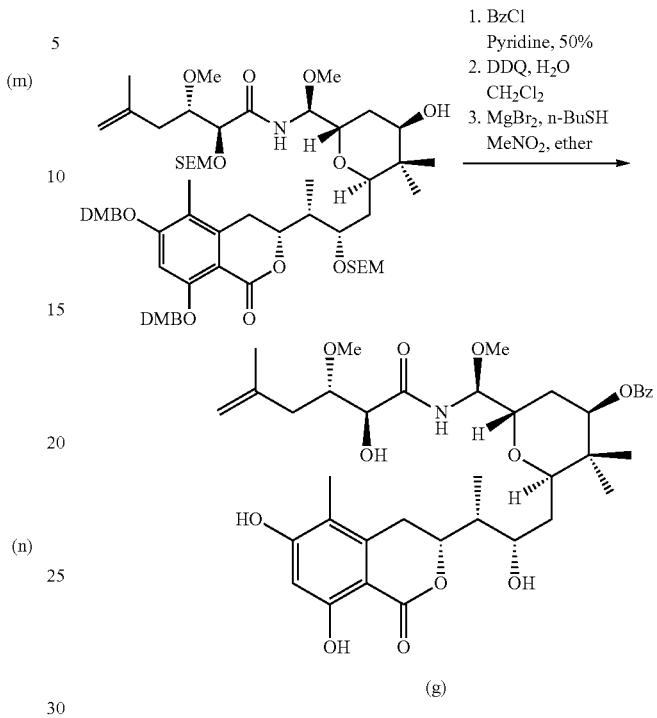

Subjecting protected alcohol (m) with acetic anhydride, followed by deprotection will result in compound (h). This is shown in Scheme 2.

Scheme 2

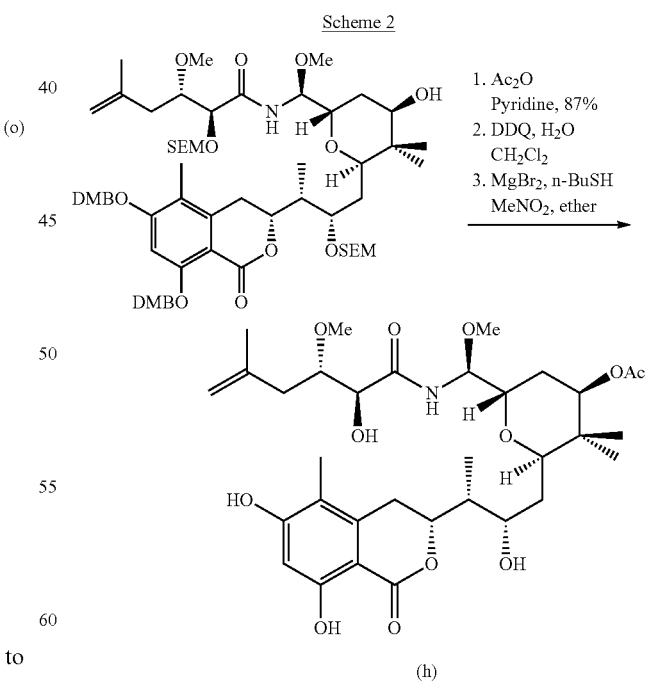

Subjecting protected alcohol (m) with trimethyloxonium tetrafluoroborate, followed by deprotection will result in compound (i). This is depicted in Scheme 3.

Scheme 3

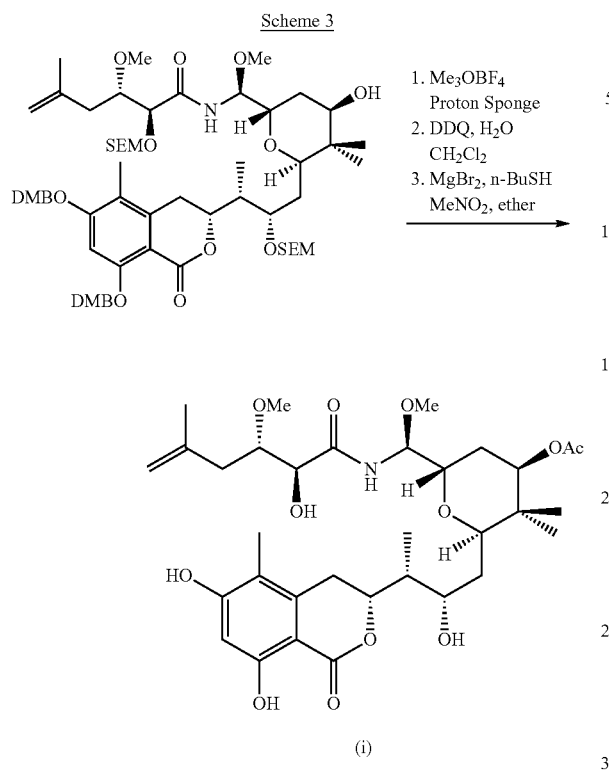

(i)

Subjecting protected alcohol (m) with diethylaminosulfur trifluoride (DAST), followed by deprotection will result in compound (j). This is shown in Scheme 4.

Scheme 4

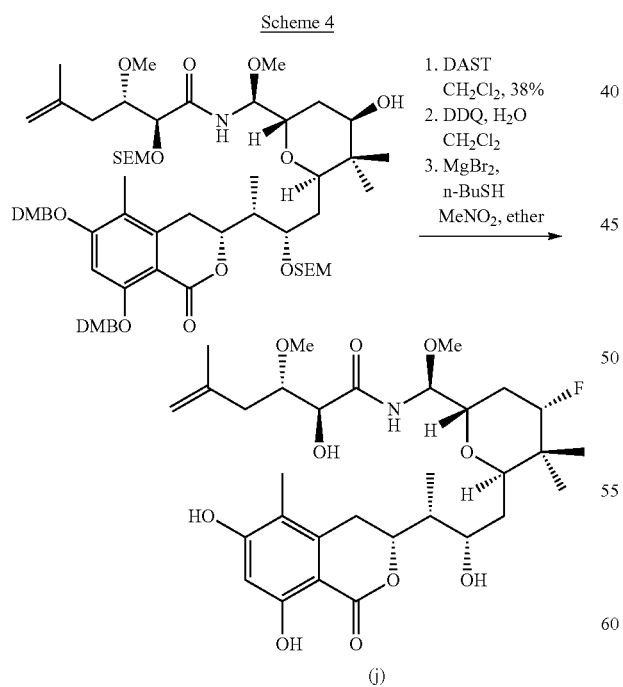

(j)

Subjecting protected alcohol (o) under Wittig conditions, followed by deprotection will result in compound (k). This is depicted in Scheme 5.

Scheme 5

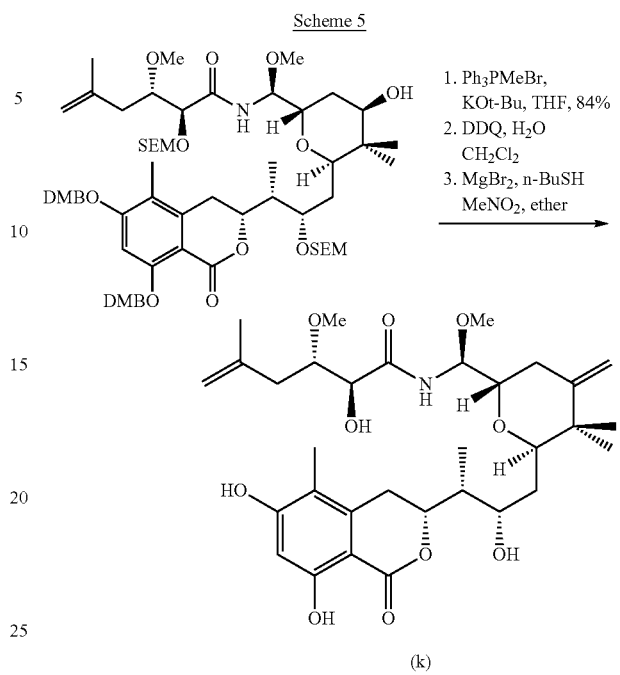

(k)

Subjecting protected alcohol (o) with O-methylhydroxylamine hydrochloride, followed by deprotection will result in compound (l). This is shown in Scheme 6.

Scheme 6

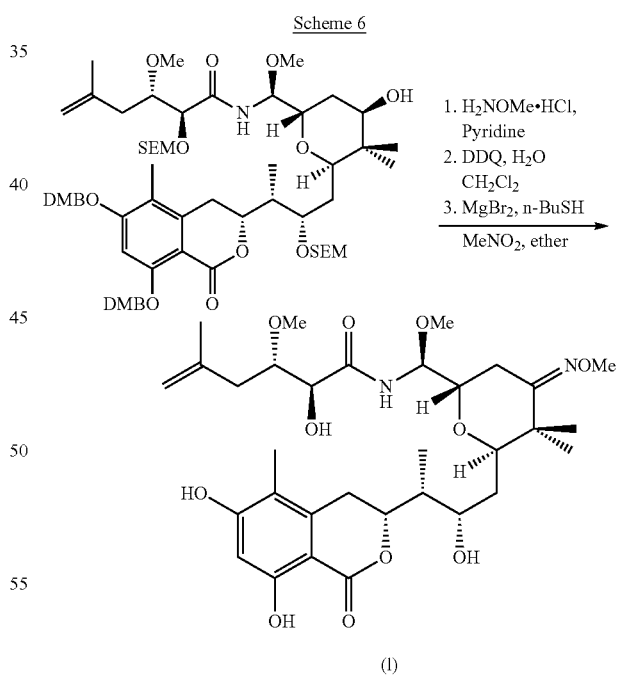

(l)

The compounds described herein may be used in pharmaceutical compositions. To prepare the pharmaceutical compositions of this invention, an effective amount of the particular compound, optionally in salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

It is especially advantageous to formulate the aforementioned pharmaceutical compositions into pharmaceutical dosage form, and in particular, in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof The exact dosage, the therapeutically effective amount and frequency of administration depends on the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

EXAMPLES

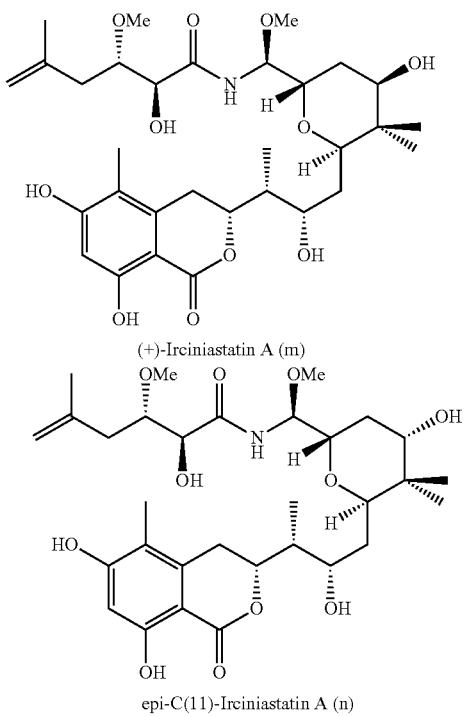

(+)-Irciniastatin A (m)

epi-C(11)-Irciniastatin A (n)

(+)-Irciniastatin A (m) and Epi-C(11)-Irciniastatin A (n):

Neat (−)-irciniastatin B (1 mg, 1.6 μmol) was treated with a solution of $NaBH_4$ (0.1 mL, 0.024 M in MeOH, 1.5 equiv) at 0° C. After 15 min, the reaction mixture was quenched with a saturated aq. solution of $NaHCO_3$ (0.4 mL) and extracted with EtOAc (3×0.5 mL). The combined organic layers were dried over $MgSO_4$, filtered and concentrated in vacuo. The crude mixture (1:1) of (+)-(m) and (n) was purified via preparatory TLC (70% EtOAc: hexanes, 250 micron $SiO_2$ plate) to provide (+)-irciniastatin A (m) (0.3 mg, 0.5 μmol 31%) and epi-C(11)-irciniastatin A (n) (0.3 mg, 0.5 μmol, 31%).

Characterization data for (+)-irciniastatin A (m): $^1H$ NMR (500 MHz, MeOD) δ 6.24 (s, 1H), 5.39 (d, J=8.3 Hz, 1H), 4.74 (s, 1H), 4.71 (s, 1H), 4.51-4.47 (ddd, J=3.0, 5.9, 12.0 Hz, 1H), 4.35 (d, J=2.6 Hz, 1H), 3.94 (m, 2H), 3.67 (ddd, J=2.6, 3.5, 9.5 Hz, 1H), 3.60 (dd, J=4.4, 10.9 Hz, 1H), 3.50 (dd, J=2.0, 10.1 Hz, 1H), 3.35 (s, 3H), 3.23 (s, 3H), 3.13 (dd, J=3.3, 16.7 Hz, 1H), 2.86 (dd, J=12.0, 16.6 Hz, 1H), 2.35 (dd, J=9.4, 14.8 Hz, 1H), 2.11 (m, 1H), 2.10 (s, 3H), 2.02 (ddd, J=2.6, 4.5, 13.4 Hz, 1H), 1.91 (m, 1H), 1.86-1.74 (m, 2H), 1.72 (s, 3H), 1.68 (ddd, J=2.1, 3.8, 14.6 Hz, 1H), 1.10 (d, J=7.1 Hz, 3H), 0.97 (s, 3H), 0.90 (s, 3H); $^{13}C$ NMR (125 MHz, $CDCl_3$) Observable peaks δ 176.3, 172.5, 163.9, 144.0, 141.2, 115.5, 113.1, 101.6, 82.8, 82.3, 82.1, 79.9, 73.6, 73.3, 72.1, 57.8 56.7, 43.4, 39.9, 38.8, 34.5, 30.6, 29.6, 23.8, 23.0, 14.0, 11.0, 9.3; HRMS (ES+) m/z 632.3033 [(M+H)+; calcd for $C_{31}H_{47}NO_{11}Na$: 632.3047].

Characterization data for epi-C(11)-irciniastatin A (n): $^1H$ NMR (500 MHz, MeOD) Observable peaks δ 6.25 (s, 1H), 5.25 (d, J=3.6 Hz, 1H), 4.76 (s, 1H), 4.73 (s, 1H), 4.51-4.47 (ddd, J=3.1, 6.8, 12.2 Hz, 1H), 4.37 (d, J=2.8 Hz, 1H), 4.04 (m, 1H), 3.97 (dd, J=4.0, 13.2 Hz, 1H), 3.78 (dd, J=3.1, 11.8 Hz, 1H), 3.73-3.67 (m, 2H), 3.33 (s, 3H), 3.17 (dd, J=3.3, 16.7 Hz, 1H), 2.83 (dd, J=11.9, 16.2 Hz, 1H), 2.35 (dd, J=9.7, 15.0 Hz, 1H), 2.12 (dd, J=3.9, 14.2 Hz, 1H), 2.09 (s, 3H), 1.96 (m, 2H), 1.79 (m, 1H), 1.73 (s, 3H), 1.63 (m, 2H), 1.12 (d, J=7.0 Hz, 3H), 1.01 (s, 3H), 0.93 (s, 3H); $^{13}$C NMR (125 MHz, CDCl$_3$) Observable peaks δ 176.0, 172.6, 164.7, 163.8, 144.0, 141.2, 115.4, 113.2, 101.5, 101.5, 83.0, 82.5, 73.0, 72.7, 72.0, 57.9, 56.7, 42.8, 39.0, 38.7, 30.9, 29.6, 23.1, 22.8, 21.3, 10.9, 9.7; HRMS (ES+) m/z 632.3029 [(M+H)$^+$; calcd for C$_{31}$H$_{47}$NO$_{11}$Na: 632.3047].

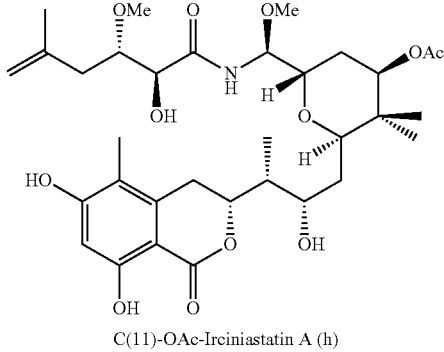

C(11)-OAc-Irciniastatin A (h)

C(11)-OAc-Irciniastatin A (h):

To a solution of fully protected C(11)-OAc-irciniastatin A (5.1 mg, 0.0042 mmol) in CH$_2$Cl$_2$ (0.05 mL) and H$_2$O (15 uL) was added a suspension of 2,3-dichloro-5,6-dicyano-1,4-benzoquinone (0.1 mL, 0.33 M in CH$_2$Cl$_2$, 8 equiv). After 10 h, the reaction mixture was quenched with a saturated aq. solution of NaHCO$_3$ and extracted with EtOAc (5×0.5 mL). The combined organic layers were dried over MgSO$_4$, filtered and concentrated in vacuo. The crude mixture was purified via flash chromatography (50% EtOAc: hexanes) to afford a mixture (1:2) of desired bis-phenol and 3,4-dimethoxybenzaldehyde respectively. The mixture was treated with a stock solution of MgBr$_2$/n-BuSH/MeNO$_2$ in Et$_2$O (0.155 mL: 25 equiv MgBr$_2$, 25 equiv nBuSH, stock solution made up of 57.4 mg MgBr$_2$, 33 µL n-BuSH, 62 µL, MeNO$_2$ and 0.62 mL Et$_2$O). After 9 h, the reaction mixture was diluted with EtOAc, and quenched with a saturated aq. solution of NaHCO$_3$ and extracted with EtOAc (5×0.5 mL). The combined organic layers were dried over MgSO$_4$, filtered and concentrated in vacuo. The crude mixture was purified via flash chromatography with SiO$_2$ [deactivated with 5% v/v triethylamine, 40% to 80% EtOAc: hexanes] to afford (+)-C(11)-OAc-irciniastatin A (h) (1.9 mg, 0.0031 mmol, 75% over two steps) as a colorless solid: [α]$_D^{20}$ +3.9 (c 0.15, CHCl$_3$); IR (neat) 3372, 2923, 2850, 1737, 1661, 1617, 1515, 1461, 1373, 1251, 1172, 1108, 1071 cm$^{-1}$; $^1$H NMR (500 MHz, CDCl$_3$) δ 11.15 (s, 1H), 7.17 (d, J=9.7 Hz, 1H), 6.59 (bs, 1H), 6.30 (s, 1H), 5.43 (dd, J=1.6, 10.3 Hz, 1H), 4.89 (dd, J=4.4, 9.3 Hz, 1H), 4.81 (s, 1H), 4.80 (s, 1H), 4.59 (ddd, J=3.8, 8.3, 11.8 Hz, 1H), 4.43 (app bs, 1H), 4.24 (app bs, 1H), 3.97-3.90 (m, 2H), 3.77-3.74 (m, 2H), 3.65 (d, J=10.5 Hz, 1H), 3.44-3.35 (m, 1H), 3.40 (s, 3H), 3.39 (s, 3H), 2.91-2.80 (m, 2H), 2.37 (dd, J=8.8, 14.6 Hz, 1H), 2.18 (dd, J=3.9, 14.8 Hz, 1H), 2.10 (s, 3H), 2.03 (s, 3H), 1.91 (m, 2H), 1.83-1.78 (m, 1H), 1.76 (s, 3H), 1.63 (d, J=15.0 Hz, 1H), 1.11 (d, J=7.1 Hz, 3H), 0.97 (s, 3H), 0.96 (s, 3H); $^{13}$C NMR (125 MHz, CDCl$_3$) δ 173.3, 170.7, 162.5, 161.1, 142.2, 140.0, 113.3, 101.9, 101.5, 82.6, 80.6, 79.4, 79.0, 74.0, 73.4, 72.8, 71.8, 58.0, 56.7, 56.1, 42.8, 37.6, 37.5, 31.9, 29.9, 28.7, 27.1, 24.1, 22.9, 21.4, 10.7, 9.6; HRMS (ES+) m/z 674.3155 [(M+Na)$^+$; calcd for C$_{33}$H$_{49}$NO$_{12}$: 674.3152].

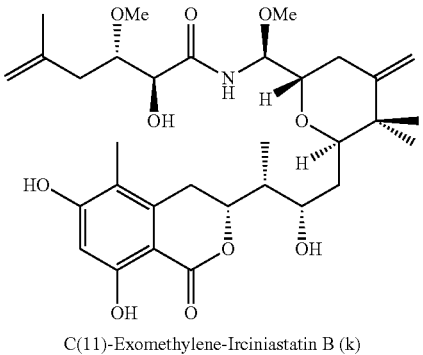

C(11)-Exomethylene-Irciniastatin B (k)

C(11)-Exomethylene-Irciniastatin B (k):

To a solution of fully protected C(11)-exomethylene-irciniastatin B (5.0 mg, 0.0043 mmol) in CH$_2$Cl$_2$ (0.05 mL) and H$_2$O (15 uL) was added a suspension of 2,3-dichloro-5,6-dicyano-1,4-benzoquinone (0.1 mL, 0.34 M in CH$_2$Cl$_2$, 8 equiv). After 11.5 h, the reaction mixture was quenched with a saturated aq. solution of NaHCO$_3$ and extracted with EtOAc (5×0.5 mL). The combined organic layers were dried over MgSO$_4$, filtered and concentrated in vacuo. The crude mixture was purified via flash chromatography (50% EtOAc: hexanes) to afford a mixture (1:2) of desired bis-phenol and 3,4-dimethoxybenzaldehyde respectively. The mixture was treated with a stock solution of MgBr$_2$/n-BuSH/MeNO$_2$ in Et$_2$O (0.200 mL: 25 equiv MgBr$_2$, 25 equiv nBuSH, stock solution made up of 42.3 mg MgBr$_2$, 18 µL n-BuSH, 46 µL, MeNO$_2$ and 0.46 mL Et$_2$O). After 10 h, the reaction mixture was diluted with EtOAc, and quenched with a saturated aq. solution of NaHCO$_3$ and extracted with EtOAc (5×0.5 mL). The combined organic layers were dried over MgSO$_4$, filtered and concentrated in vacuo. The crude mixture was purified via flash chromatography with SiO$_2$ [deactivated with 5% v/v triethylamine, 40% to 80% EtOAc: hexanes] to afford (+)-C(11)-exomethylene-irciniastatin A (k) (2.0 mg, 0.0033 mmol, 77% over two steps) as a colorless solid: [α]$_D^{20}$ +12.7 (c 0.17, CHCl$_3$); IR (neat) 3379, 2921, 1732, 1659, 1623, 1514, 1454, 1379, 1254, 1109 cm$^{-1}$; $^1$H NMR (500 MHz, CDCl$_3$) δ 11.15 (s, 1H), 7.28 (d, J=6.7, 10.3 Hz, 1H), 6.68 (bs, 1H), 6.30 (s, 1H), 5.28 (dd, J=6.7, 10.3 Hz, 1H), 4.87 (s, 2H), 4.81 (s, 1H), 4.79 (s, 1H), 4.52 (ddd, J=4.0, 8.0, 16.4 Hz, 1H), 4.45 (d, J=3.0 Hz, 1H), 4.01 (d, J=10.1 Hz, 1H), 3.92-3.88 (m, 2H), 3.77-3.74 (ddd, J=3.8, 9.4, 12.7 Hz, 1H), 3.63 (d, J=10.7 Hz, 1H), 3.40 (s, 3H), 3.35 (s, 3H), 3.34-3.31 (m, 1H), 2.93-2.80 (m, 2H), 2.52 (dd, J=5.4, 14.2 Hz, 1H), 2.42-2.35 (m, 2H), 2.16 (dd, J=3.9, 14.8 Hz, 1H), 2.02 (s, 3H), 1.88 (m, 1H), 1.79 (dd, J=2.8, 10.6 Hz, 1H), 1.75 (3H, s), 1.55 (d, J=14.5 Hz, 1H), 1.14 (s, 3H), 1.10 (d, J=7.0 Hz, 3H), 1.06 (s, 3H); $^{13}$C NMR (125 MHz, CDCl$_3$) δ 173.3, 170.7, 162.5, 161.2, 148.2, 142.2, 140.0, 113.4, 113.2, 110.0, 101.7, 101.5, 83.4, 80.6, 80.2, 79.1, 73.9, 73.2, 72.7, 58.0, 56.5, 43.0, 39.9, 37.5, 33.0, 32.1, 28.5, 25.0, 22.9, 21.7, 10.7, 9.5; HRMS (ES$^-$) m/z 606.3280 [(M–H)$^-$; calcd for C$_{32}$H$_{48}$NO$_{10}$: 606.3278].

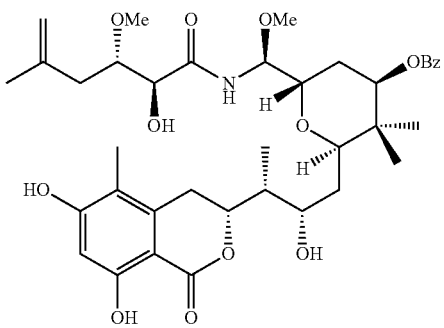
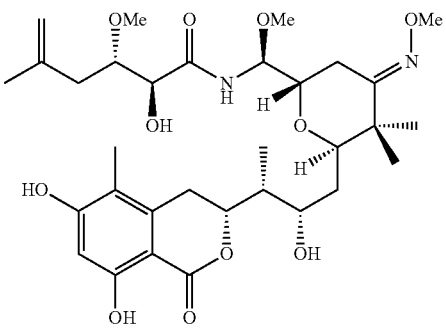

C(11)-OBz-Irciniastatin A (−)-3.6:

To a solution of fully protected benzoate (+)-S2 (3.6 mg, 0.0028 mmol) in $CH_2Cl_2$ (100 µL) and $H_2O$ (18 µL) was added a suspension of 2,3-dichloro-5,6-dicyano-1,4-benzoquinone (80 µL, 0.29 M in $CH_2Cl_2$, 8 equiv). After 10 h, the reaction mixture was quenched with a saturated aq. solution of $NaHCO_3$ and extracted with EtOAc (5×0.5 mL). The combined organic layers were dried over $MgSO_4$, filtered and concentrated in vacuo. The crude mixture was purified via flash chromatography on $SiO_2$ (50% EtOAc: hexanes) to afford a mixture (1:2) of the desired bis-phenol and 3,4-dimethoxybenzaldehyde respectively. The mixture was treated with a stock solution of $MgBr_2$/n-BuSH/$MeNO_2$ in $Et_2O$ (0.140 mL: 25 equiv $MgBr_2$, 25 equiv n-BuSH, stock solution made up of 89.9 mg $MgBr_2$, 36 µL n-BuSH, 100 µL, $MeNO_2$ and 0.98 mL $Et_2O$). After 9.5 h, the reaction mixture was diluted with EtOAc, and quenched with a saturated aq. solution of $NaHCO_3$ and extracted with EtOAc (5×0.5 mL). The combined organic layers were dried over $MgSO_4$, filtered and concentrated in vacuo. The crude mixture was purified via flash chromatography on $SiO_2$ (40% to 50% EtOAc: hexanes) to afford (−)-C(11)-OBz-irciniastatin A (43.6 (1.0 mg, 0.0014 mmol, 50% over two steps) as a colorless solid: $[\alpha]_D^{20}$ −13.7 (c 0.08, $CH_2Cl_2$); IR (neat) 3372, 2943, 1726, 1663, 1599, 1446, 1377, 1253, 1114 $cm^{-1}$; $^1$H NMR (500 MHz, $C_6D_6$) δ 11.93 (bs, 1H), 8.17 (d, J=7.5 Hz, 3H), 7.10 (t, J=7.5 Hz, 2H), 6.31 (s, 1H), 5.67 (t, J=8.3 Hz, 1H), 5.27 (dd, J=4.4, 9.9 Hz, 1H), 5.04 (s, 1H), 4.92 (s, 1H), 4.61 (bs, 1H), 4.33 (m, 3H), 4.17 (d, J=9.7 Hz, 1H), 3.91 (ddd, J=3.5, 3.5, 4.0 Hz, 1H), 3.73 (d, J=10.4 Hz, 1H), 3.59 (bs, 1H), 3.32 (s, 3H), 3.25 (s, 3H), 2.63 (d, J=16.3 Hz, 1H), 2.65-2.51 (ddd, J=8.7, 12.4, 12.4 Hz, 1H), 2.46 (dd, J=4.6, 14.0 Hz, 2H), 2.26 (m, 1H), 2.02 (s, 3H), 1.93 (m, 1H), 1.79 (s, 3H), 1.58 (bs, 1H), 1.46 (d, J=13.9 Hz, 1H), 1.06 (d, J=6.6 Hz, 3H), 0.96 (s, 3H), 0.79 (s, 3H); $^{13}$C NMR (125 MHz, C6D6) δ 173.7, 170.9, 165.7, 163.2, 161.8, 142.6, 140.1, 133.2, 130.9, 129.9, 128.8, 127.5, 113.6, 113.5, 102.0, 101.6, 82.2, 81.5, 80.1, 78.9, 74.3, 73.8, 73.5, 57.8, 56.3, 43.1, 38.1, 37.8, 33.0, 32.4, 30.2, 30.1, 28.4, 27.2, 23.1, 14.4, 10.6, 9.2; HRMS (ES+) m/z 736.3286 [(M+Na)$^+$; calcd for $C_{38}H_{51}NO_{12}Na$: 736.3309].

C(11)-O-Methyloxime-Irciniastatin B (+)-3.10:

To a solution of O-methyloxime (+)-S5 (4.9 mg, 0.0041 mmol) in $CH_2Cl_2$ (0.160 mL) and $H_2O$ (26 µL) was added a suspension of 2,3-dichloro-5,6-dicyano-1,4-benzoquinone (0.1 mL, 0.33 M in $CH_2Cl_2$, 8 equiv). After 11 h, the reaction mixture was quenched with a saturated aq. solution of $NaHCO_3$ and extracted with EtOAc (3×0.5 mL). The combined organic layers were dried over $MgSO_4$, filtered and concentrated in vacuo to afford a mixture (1:2) of desired bis-phenol and 3,4-dimethoxybenzaldehyde respectively. The crude mixture was carried forward without further purification.

The mixture of bis-phenol and 3,4-dimethoxybenzaldehyde (1:2 mixture) was treated with a stock solution of $MgBr_2$/n-BuSH/$MeNO_2$ in $Et_2O$ (0.200 mL: 25 equiv $MgBr_2$, 25 equiv n-BuSH, stock solution made up of 47.4 mg $MgBr_2$, 28 µL n-BuSH, 50 µL, $MeNO_2$ and 0.52 mL $Et_2O$). After 10 h, the reaction mixture was diluted with EtOAc, and quenched with a saturated aq. solution of $NaHCO_3$ and extracted with EtOAc (5×0.5 mL). The combined organic layers were dried over $MgSO_4$, filtered and concentrated in vacuo. The crude mixture was purified via flash chromatography with water washed $SiO_2$ [50 g of $SiO_2$ washed with $H_2O$ (500 mL) then MeOH (500 mL) then EtOAc (500 mL) then hexanes (500 mL) and dried under vacuum overnight, then deactivated with 5% v/v triethylamine, 30% to 50% to 70% EtOAc: hexanes] to afford (+)-C(11)-O-methyloxime-irciniastatin B (+)-3.10 (1.6 mg, 0.0025 mmol, 61% over two steps) as a colorless solid: $[\alpha]_D^{20}$ +24.8 (c 0.14, $CH_2Cl_2$); IR (neat) 3370, 2920, 2857, 1658, 1262, 1171, 1071 $cm^{-1}$; $^1$H NMR (500 MHz, $CDCl_3$) δ 11.12 (s, 1H), 7.32 (d, J=10.0 Hz, 1H), 6.30 (s, 1H), 5.49 (bs, 1H), 5.13 (dd, J=6.8, 10.2 Hz, 1H), 4.81 (s, 1H), 4.78 (s, 1H), 4.52 (ddd, J=3.9, 3.9, 11.2 Hz, 1H), 4.45 (d, J=2.7 Hz, 1H), 4.03 (d, J=2.7 Hz, 1H), 3.97 (dt, J=6.2, 12.5 Hz, 1H), 3.86 (s, 3H), 3.78-3.76 (ddd, J=3.5, 3.5, 9 Hz, 1H), 3.73 (d, J=11.3 Hz, 2H), 3.39 (s, 3H), 3.36 (s, 3H), 2.91-2.80 (m, 3H), 2.70 (dd, J=5.3, 14.7 Hz, 1H), 2.37 (dd, J=9.4, 14.7 Hz, 1H), 2.14 (dd, J=3.7, 14.8 Hz, 1H), 2.09 (s, 3H), 1.89 (m, 2H), 1.80 (dd, J=10.8, 15.0 Hz, 1H), 1.75 (s, 3H), 1.59 (d, J=15.0 Hz, 1H), 1.18 (s, 3H), 1.12 (app s, 3H), 1.10 (s, 3H); $^{13}$C NMR (125 MHz, $CDCl_3$) δ 173.3, 170.8, 162.4, 161.4, 158.0, 142.1, 139.9, 113.5, 113.3, 101.5, 83.5, 80.5, 80.4, 79.9, 73.1, 72.7, 72.4, 61.7, 57.9, 56.9, 42.8, 40.7, 37.5, 32.4, 32.1, 29.9, 28.4, 23.7, 22.8, 20.9, 10.7, 9.2; HRMS (ES$^-$) m/z 659.3156 [(M+Na)$^+$; calcd for $C_{32}H_{48}N_2O_{11}Na$: 659.3156].

Biological Activity

The above described compositions will be bioactive. The compounds will be biologically assayed by testing for their antitumor activity with various cell lines. The $IC_{50}$ will be used to evaluate the activity as described in Huang, X.;

Shao, N.; Huryk, R.; Palani, A.; Aslanian, R.; Seidel-Dugan, C. *Org. Lett.* 2009, 11, 867-870 or Wu, C. Y.; Feng, Y.; Cardenas, E. R.; Williams, N.; Floreancig, P. E.; De Brabander, J. K.; Roth, M. G. *J. Am. Chem. Soc.* 2012, 134, 18998-19003. For example, the CellTiter-Glo Luminescent Cell Viability Assay may be employed as the biological assay.

Cell Culture and Cell Growth Inhibition Assay.

The chosen cell lines are all human cancer cell lines except for the 4T1 murine breast cancer line, representing a wide variety of cancer types including breast (MDA-MB-453), kidney (A498), lung (H1975), pancreatic (PANC-1) and endometrial cancer (AN3CA, HEC-1A, and RL95-2), glioblastoma (U251 and U-87MG), melanoma (A2058 and LOXIMVI) and uterine sarcoma (MES-SA). All the cancer cell lines can be obtained from the American Type Culture Collection (ATCC, Manassas, Va., USA) with the exception of U251 which can be provided by the National Cancer Institute Tumor Repository (Frederick, Md.) and is cultured in the standard tissue culture media appropriate for each cell line. All the culture media are supplemented with 10% fetal bovine serum (FBS), 100 I.U./mL penicillin and 100 μg/mL streptomycin. For the cell growth inhibition assay, the cells are seeded in 96-well tissue culture plates at 500-3000 cells/well (seeding density empirically adjusted for each cell line based on growth rate optimization). The cells are allowed to attach for a minimum of 5 h prior to compound administration. The cells are incubated for a period of 4 days after compound addition. Following the incubation period, CellTiter-Glo reagent (Promega, Madison, Wis., USA) is added to all the wells to assess cell proliferation/viability. Luminescence is measured using an Envision microplate reader (Perkin Elmer, Waltham, Mass., USA). The IC50 values were calculated as the concentration which inhibited cell growth to 50% of DMSO control treated cell populations.

IMR-90 Cytotoxicity Assay.

To evaluate the effect of compounds of the invention on non-proliferating normal cells, an in vitro cytotoxicity assay developed to distinguish between true antiproliferative activity and general cellular cytotoxicity unrelated to proliferation was used. Rudolph-Owen L A, Salvato K, Cheng C, Wu J, Towle M J and Littlefield B A: A 96-well plate cell-based assay to quantify undesired cytotoxic effects against quiescent non-dividing cells. Proc Amer Assoc Cancer Res 45: 264-265, 2004. In brief, IMR-90 human fibroblast cells, obtained from ATCC, were grown for 4 days to confluency in MEM containing 10% FBS and supplemented with L-glutamine, penicillin/streptomycin. After washing, the medium was replaced with complete MEM containing 0.1% FBS and the cells were cultured for 3 additional days to achieve complete quiescence. A compound of the invention or vehicle control was then added in the continued presence of 0.1% FBS, followed by incubation for 3 days at 37° C. Cell viability was assessed by the measurement of cellular ATP levels using CellTiter-Glo reagent (Promega).

Biological data for certain embodiments of the invention is set forth in the table below.

| Name | Structure | $IC_{50}$ (nM) Selectivity vs. IMR-90 | | | |
|---|---|---|---|---|---|
| | | A2058 | H522-T1 | HCT-116 | Quiescent IMP-90 |
| Irciniastatin B | [structure] | 0.5 / 114* | 0.8 / 71* | 3 / 19* | 57 |
| Irciniastatin A | [structure] | 0.4 / 68* | 1 / 27* | 4 / 7* | 27 |

| Name | Structure | IC$_{50}$ (nM) Selectivity vs. IMR-90 | | | |
|---|---|---|---|---|---|
| | | A2058 | H522-T1 | HCT-116 | Quiescent IMP-90 |
| epi-C(11)-Irciniastatin A | 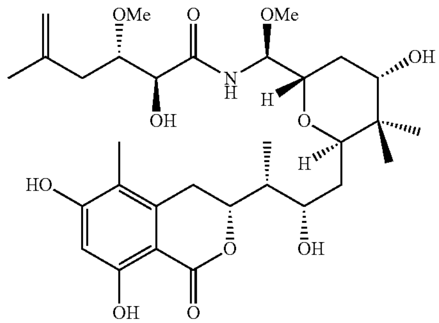 | 0.4 85* | 0.9 38* | 3 11* | 34 |
| C(11)-OAc-Irciniastatin A | 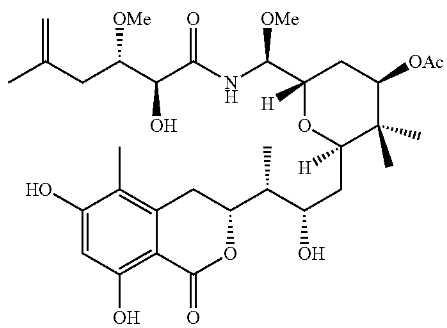 | 0.4 68* | 0.7 39* | 2 14* | 27 |
| C(11)-Exomethylene-Irciniastatin B | 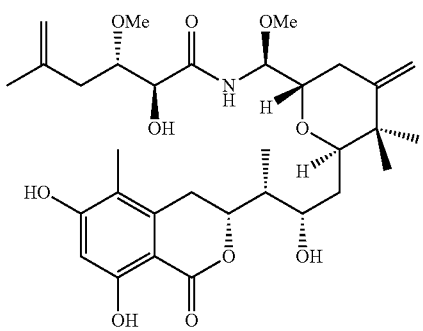 | 0.7 70* | 1.6 31* | 1 49* | 49 |
| C(11)-Obz-Irciniastatin A | 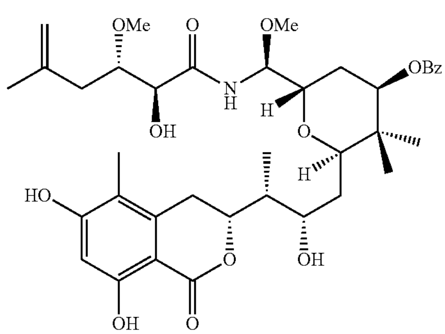 | 2.7 30* | 5.4 15* | | 81 |

| Name | Structure | IC$_{50}$ (nM) Selectivity vs. IMR-90 | | | |
|---|---|---|---|---|---|
| | | A2058 | H522-T1 | HCT-116 | Quiescent IMP-90 |
| C(11)-O-Methyloxime-Irciniastatin B | 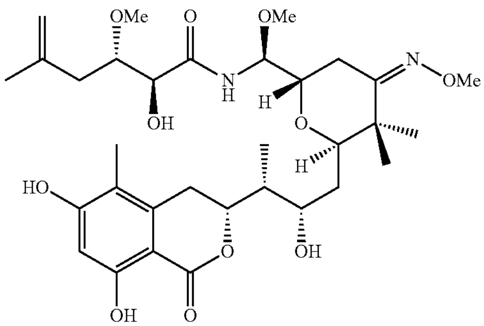 | 0.5 92* | 0.8 58* | | 46 |

*Number refers to the selectivity value for anti-proliferative activity for a cell line versus indiscriminate cytotoxicity against quiescent IMR-90 cells and is defined by the ratio IC$_{50}$[IMR-90]:IC$_{50}$[tumor cell line].

The general description and the above detailed description are exemplary and explanatory only and are not restrictive of the invention, as defined in the appended claims. Other aspects of the present invention will be apparent to those skilled in the art in view of the detailed description of the invention as provided herein.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

When ranges are used herein for physical properties, such as molecular weight, or chemical properties, such as chemical formulae, all combinations, and subcombinations of ranges for specific embodiments therein are intended to be included.

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A compound of Formula I, or a stereoisomer thereof,

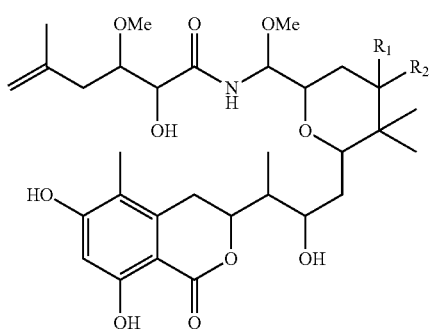

I wherein

R$_1$ is hydrogen; and

R$_2$ is halogen, O—C(O)phenyl, O—C(O)C$_{1-6}$alkyl, or C$_{1-6}$ alkyl, or wherein R$_1$ and R$_2$ together form =CR$_3$R$_4$ or =NR$_5$ wherein R$_3$ and R$_4$ are independently hydrogen or C$_{1-6}$ alkyl, and R$_5$ is O—C$_{1-6}$ alkyl;

or a pharmaceutically acceptable salt thereof.

2. The compound of claim 1, or a stereoisomer thereof, wherein R$_2$ is halogen.

3. The compound of claim 2, or a stereoisomer thereof, wherein R$_2$ is F.

4. The compound of claim 1, or a stereoisomer thereof, wherein R$_2$ is —OC(O)phenyl.

5. The compound of claim 1, or a stereoisomer thereof, wherein R$_2$ is —OC(O)C$_{1-6}$alkyl.

6. The compound of claim 5, or a stereoisomer thereof, wherein R$_2$ is

—OC(O)CH$_3$.

7. The compound of claim 1, or a stereoisomer thereof, wherein R$_2$ is

—C$_{1-6}$alkyl.

8. The compound of claim 1, or a stereoisomer thereof, wherein R$_1$ and R$_2$ together are =CR$_3$R$_4$.

9. The compound of claim 8, or a stereoisomer thereof, wherein R$_3$ and R$_4$ are each hydrogen.

10. The compound of claim 8, or a stereoisomer thereof, wherein R$_3$ and R$_4$ are each C$_{1-6}$alkyl.

11. The compound of claim 8, or a stereoisomer thereof, wherein R$_3$ and R$_4$ are independently hydrogen and C$_{1-6}$alkyl.

12. The compound claim 1, or a stereoisomer thereof, wherein R$_1$ and R$_2$ together are =NR$_5$.

13. The compound of claim 12, or a stereoisomer thereof, wherein R$_5$ is —OCH$_3$.

14. The compound of claim 1, or a stereoisomer thereof, wherein the compound is

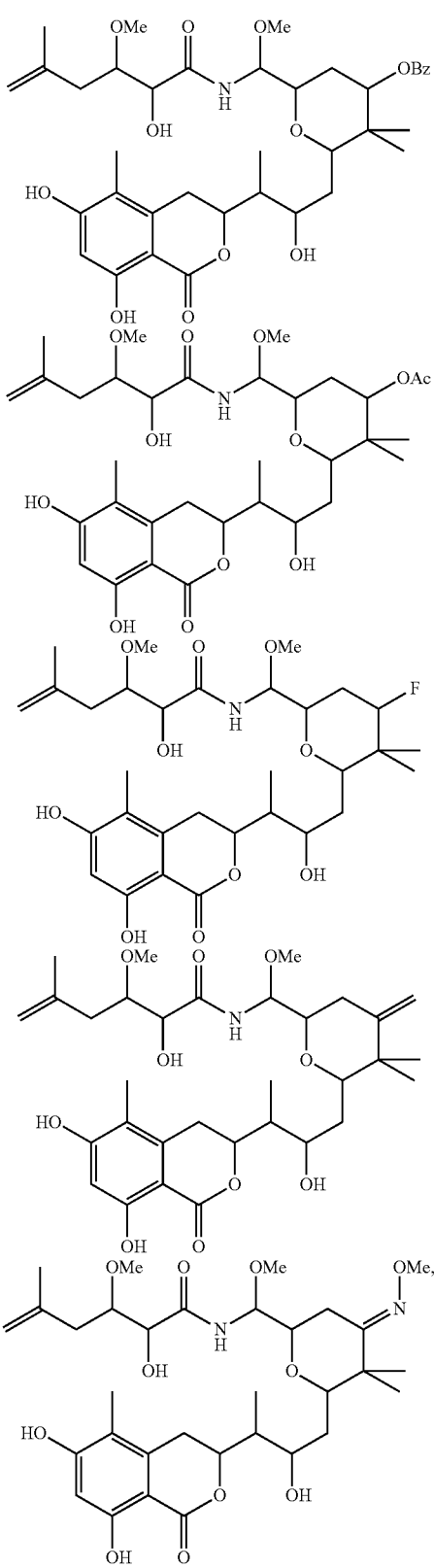

or a pharmaceutically acceptable salt thereof.

15. The compound of claim 1, or a stereoisomer thereof, wherein the compound is

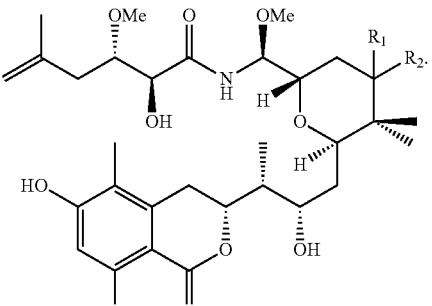

16. The compound of claim 1, wherein the compound is

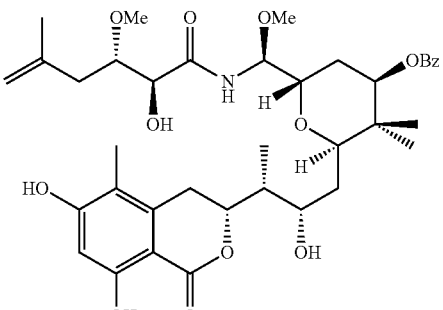

or a pharmaceutically acceptable salt thereof.

17. The compound of claim 1, wherein the compound is

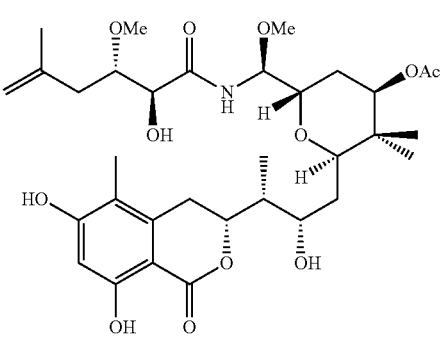

or a pharmaceutically acceptable salt thereof.

18. The compound of claim 1, wherein the compound is

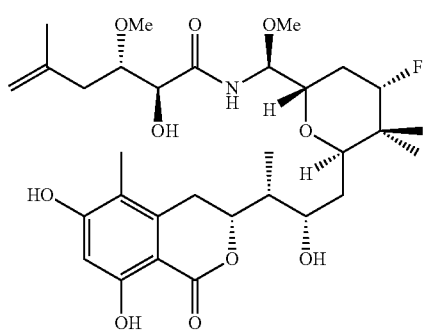

or a pharmaceutically acceptable salt thereof.

19. The compound of claim 1, wherein the compound is
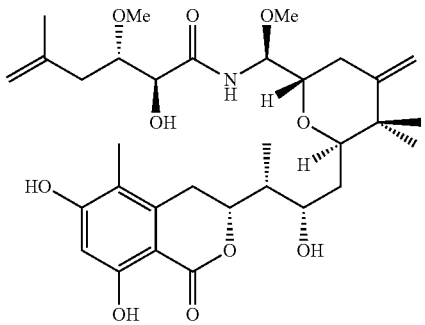
or a pharmaceutically acceptable salt thereof.
20. The compound of claim 1, wherein the compound is
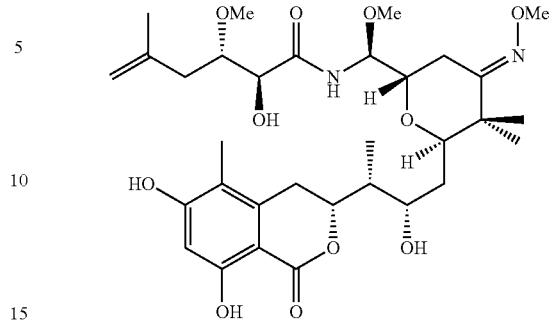
or a pharmaceutically acceptable salt thereof.
21. A pharmaceutical composition comprising a compound according to claim 1 and a pharmaceutically acceptable carrier or diluent.
* * * * *

UNITED STATES PATENT AND TRADEMARK OFFICE
CERTIFICATE OF CORRECTION

PATENT NO. : 9,540,355 B2
APPLICATION NO. : 14/761030
DATED : January 10, 2017
INVENTOR(S) : Amos B. Smith et al.

Page 1 of 1

It is certified that error appears in the above-identified patent and that said Letters Patent is hereby corrected as shown below:

In the Specification

Column 1, Lines 14-18, delete "The subject matter disclosed herein was made with government support under the National Institutes of Health (National Cancer Institute) under Grant No. CA-19033. The Government has certain rights in the herein disclosed subject matter." and insert -- This invention was made with government support under grant number CA019033 awarded by the National Institutes of Health. The government has certain rights in the invention. --.

Signed and Sealed this
Fifth Day of February, 2019

Andrei Iancu
*Director of the United States Patent and Trademark Office*